(12) United States Patent
Banning et al.

(10) Patent No.: US 7,345,200 B2
(45) Date of Patent: Mar. 18, 2008

(54) PHASE CHANGE INK FORMULATIONS, COLORANT FORMULATIONS, AND METHODS OF FORMING COLORANTS

(75) Inventors: Jeffrey H. Banning, Hillsboro, OR (US); Michael B. Meinhardt, Salem, OR (US); Donald R. Titterington, Tualatin, OR (US); Clifford R. King, Salem, OR (US)

(73) Assignee: Xerox Corporation, Norwalk, CT (US)

( * ) Notice: Subject to any disclaimer, the term of this patent is extended or adjusted under 35 U.S.C. 154(b) by 0 days.

(21) Appl. No.: 11/355,428

(22) Filed: Feb. 16, 2006

(65) Prior Publication Data

US 2006/0161009 A1 Jul. 20, 2006

Related U.S. Application Data

(60) Division of application No. 09/772,617, filed on Jan. 30, 2001, now Pat. No. 7,022,879, which is a division of application No. 09/397,348, filed on Sep. 15, 1999, now Pat. No. 6,235,094, which is a continuation-in-part of application No. 09/023,851, filed on Feb. 13, 1998, now Pat. No. 6,028,138, which is a continuation-in-part of application No. 08/672,815, filed on Jun. 28, 1996, now Pat. No. 5,830,942, and a continuation-in-part of application No. 09/013,410, filed on Jan. 26, 1998, now Pat. No. 5,994,453.

(51) Int. Cl.
*C07C 233/11* (2006.01)
(52) U.S. Cl. .................. 564/163; 564/168
(58) Field of Classification Search .......... 564/163, 564/168
See application file for complete search history.

(56) References Cited

U.S. PATENT DOCUMENTS

| | | | |
|---|---|---|---|
| 2,409,712 A | 12/1946 | Schweitzer | |
| 3,012,991 A | 12/1961 | Schultheis et al. | |
| 3,384,623 A | 5/1968 | Inoue et al. | |
| 3,425,973 A | 2/1969 | Shaw, Jr. | |
| 3,653,932 A | 4/1972 | Berry et al. | |
| 3,963,679 A | 6/1976 | Ullrich et al. | |
| 3,963,710 A | 6/1976 | Aufdermarsh, Jr. | |
| 4,011,311 A | 3/1977 | Noomen et al. | |
| 4,080,314 A | 3/1978 | Bonk et al. | |
| 4,284,729 A | 8/1981 | Cross et al. | |
| 4,293,470 A | 10/1981 | Cuscurida | |
| 4,297,501 A | 10/1981 | Becker et al. | |
| 4,334,032 A | 6/1982 | Patton, Jr. et al. | |
| 4,381,403 A | 4/1983 | Falcone et al. | |
| 4,390,369 A | 6/1983 | Merritt et al. | |
| 4,484,948 A | 11/1984 | Merritt et al. | |
| 4,501,915 A | 2/1985 | McCoy | |
| 4,537,960 A | 8/1985 | Merger et al. | |
| 4,574,147 A | 3/1986 | Meckel | |
| 4,647,675 A | 3/1987 | Mayer et al. | |

(Continued)

FOREIGN PATENT DOCUMENTS

DE 4205636 8/1993

(Continued)

OTHER PUBLICATIONS

"Polymer Chemistry—The Basic Concepts" by Paul C. Hiemenz, California State Polytechnic University, Pomona, California, p. 7.

(Continued)

*Primary Examiner*—Rebecca Anderson
(74) *Attorney, Agent, or Firm*—Judith L. Byorick

(57) ABSTRACT

A compound having the formula

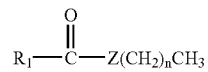

wherein $R_1$, Z, and the carbonyl can be comprised by a common ring, wherein $R_1$ comprises a chromophore that absorbs light from the visible wavelength range, and wherein n is an integer of at least 12. A solid phase change ink composition is also disclosed containing a colorant comprising a chromophore that absorbs light from the visible wavelength range and has the formula

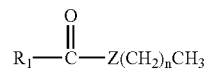

wherein $R_1$, Z, and the carbonyl can be comprised by a common ring, and wherein n is an integer of at least 12. Also disclosed is a method of forming a colorant wherein a first compound having the formula

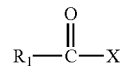

is reacted with a second compound having the formula $Z(CH_2)_nCH_3$ wherein n is an integer of at least 12 to form a third compound having the formula

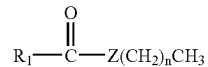

wherein the third compound comprises a chromophore that absorbs light from the visible wavelength range.

6 Claims, 3 Drawing Sheets

U.S. PATENT DOCUMENTS

| | | | |
|---|---|---|---|
| 4,665,146 | A | 5/1987 | Tortorello et al. |
| 4,684,956 | A | 8/1987 | Ball |
| 4,810,820 | A | 3/1989 | Slack et al. |
| 4,846,846 | A | 7/1989 | Rekers et al. |
| 4,851,045 | A | 7/1989 | Taniguchi |
| 4,889,560 | A | 12/1989 | Jaeger et al. |
| 4,889,761 | A | 12/1989 | Titterington et al. |
| 5,006,170 | A | 4/1991 | Schwarz et al. |
| 5,059,647 | A | 10/1991 | Kawaguchi |
| 5,151,120 | A | 9/1992 | You et al. |
| 5,195,430 | A | 3/1993 | Rise |
| 5,221,335 | A | 6/1993 | Williams et al. |
| 5,231,135 | A | 7/1993 | Machell et al. |
| 5,278,223 | A | 1/1994 | Gruenewaelder et al. |
| 5,372,852 | A | 12/1994 | Titterington et al. |
| 5,389,720 | A | 2/1995 | Markusch et al. |
| 5,389,958 | A | 2/1995 | Bui et al. |
| 5,496,879 | A | 3/1996 | Griebel et al. |
| 5,621,022 | A | 4/1997 | Jaeger et al. |
| 5,624,483 | A | 4/1997 | Fujioka |
| 5,817,860 | A | 10/1998 | Rizk et al. |
| 5,830,942 | A | 11/1998 | King et al. |
| 5,994,453 | A | 11/1999 | Banning et al. |
| 6,018,005 | A | 1/2000 | Banning et al. |
| 6,028,138 | A | 2/2000 | Hahn et al. |
| 6,048,925 | A | 4/2000 | Titterington et al. |

FOREIGN PATENT DOCUMENTS

| | | |
|---|---|---|
| EP | 0187352 | 7/1986 |
| EP | 0206286 | 12/1986 |
| WO | 94/04619 | 3/1994 |
| WO | 94/14902 | 7/1994 |

OTHER PUBLICATIONS

"Technical Product Information" Luxate IM Isophorone Diisocyanate, by Olin Chemicals, Olin Corporation, 2 Pages.

"Advanced Organic Chemistry—Reactions, Mechanisms, and Structure", Third Edition, by Jerry March, Professor of Chemistry, Adelphi University, 6 pages.

Patent Application entitled "Urethane Isocyanate-Derived Resins for Use in a Phase Change Ink Formulation", U.S. Appl. No. 09/240,444.

Abstract No. 194038h, Chemical Abstracts Service: Colorants and Dyes, Mar. 26, 1992.
Abstract No. 328495y, Chemical Abstracts Service: Colorants and Dyes, Jul. 4, 1994.
Abstract No. 127632w, Chemical Abstracts Service: Colorants and Dyes, Sep. 13, 1993.
Abstract No. 58182q, Chemical Abstracts Service: Colorants and Dyes, Nov. 6, 1992.
Abstract No. 148692b, Chemical Abstracts Service: Colorants and Dyes, 1995.
Abstract No. 120115a, Chemical Abstracts Service: Colorants and Dyes, Apr. 14, 1994.
Abstract No. 10580k, Chemical Abstracts Service: Colorants and Dyes, Sep. 3, 1996.
Abstract No. 196914p, Chemical Abstracts Service: Colorants and Dyes, 1996.
Abstract No. 101733a, Chemical Abstracts Service: Colorants and Dyes, Oct. 10, 1995.
Abstract No. 282312u, Chemical Abstracts Service: Colorants and Dyes, Nov. 12, 1992.
Abstract No. 349036t, Chemical Abstracts Service: Colorants and Dyes, Apr. 1, 1997.
Abstract No. 267765a, Chemical Abstracts Service: Colorants and Dyes, Sep. 4, 1992.
Abstract No. 231731s, Chemical Abstracts Service: Colorants and Dyes, Mar. 6, 1997.
Abstract No. 162781q, Chemical Abstracts Service: Colorants and Dyes, Jan. 15, 1997.
Abstract No. 258399b, Chemical Abstracts Service: Colorants and Dyes, Sep. 4, 1996.
Abstract No. 231581t, Chemical Abstracts Service: Colorants and Dyes, Aug. 12, 1996.
Abstract No. 316875p, Chemical Abstracts Service: Colorants and Dyes, Feb. 11, 1994.
Abstract No. 205869y, Chemical Abstracts Service: Colorants and Dyes, May 3, 1996.
Abstract No. 127687t, Chemical Abstracts Service: Colorants and Dyes, Aug. 25, 1993.
Abstract No. 59042w, Chemical Abstracts Service: Colorants and Dyes, May 6, 1997.
Abstract No. 67744s, Chemical Abstracts Service: Colorants and Dyes, May 12, 1997.
Abstract No. 53652y, Chemical Abstracts Service: Colorants and Dyes, May 30, 1997.
Abstract No. 257837m, Chemical Abstracts Service: Colorants and Dyes, Dec. 2, 1992.
Abstract No. 303055e, Chemical Abstracts Service: Colorants and Dyes, Oct. 31, 1992.
Abstract No. 69508f, Chemical Abstracts Service: Colorants and Dyes, Aug. 10, 1992.
Abstract No. 312084r, Chemical Abstracts Service: Colorants and Dyes, Dec. 24, 1992.
Abstract No. 6135K, Chemical Abstracts Service: Colorants and Dyes, Oct. 12, 1995.
Abstract No. 289936z, Chemical Abstracts Service: Colorants and Dyes, Mar. 13, 1997.
Abstract No. 23963w, Chemical Abstracts Service: Colorants and Dyes, Jul. 27, 1995.
Abstract No. 255366g, Chemical Abstracts Service: Colorants and Dyes, Feb. 14, 1996.
Abstract No. 193737p, Chemical Abstracts Service: Colorants and Dyes, Jun. 5, 1996.
Abstract No. 123781v, Chemical Abstracts Service: Colorants and Dyes, 1997.
Abstract No. 35960f, Chemical Abstracts Service: Colorants and Dyes, Oct. 19, 1995.
Abstract No. 111509v, Chemical Abstracts Service: Colorants and Dyes, Jun. 13, 1997.
Abstract No. 90929h, Chemical Abstracts Service: Colorants and Dyes, Jan. 31, 1992.
Abstract No. 198614c, Chemical Abstracts Service: Colorants and Dyes, Nov. 4, 1993.
Abstract No. 170874e, Chemical Abstracts Service: Colorants and Dyes, Aug. 7, 1989.
Abstract No. 247415r, Chemical Abstracts Service: Colorants and Dyes, Jun. 3, 1991.
Abstract No. 85720z, Chemical Abstracts Service: Colorants and Dyes, Oct. 1, 1992.
Abstract No. 174226e, Chemical Abstracts Service: Colorants and Dyes, Jul. 1, 1996.
Abstract No. 117709g, Chemical Abstracts Service: Colorants and Dyes, Jun. 10, 1997.
Abstract No. 274653c, Chemical Abstracts Service: Colorants and Dyes, May 31, 1994.
Abstract No. 82275s, Chemical Abstracts Service: Colorants and Dyes, May 17, 1996.
Abstract No. 131652r, Chemical Abstracts Service: Colorants and Dyes, Mar. 11, 1994.
Abstract No. 283486f, Chemical Abstracts Service: Colorants and Dyes, Mar. 17, 1997.
Abstract No. 154760s, Chemical Abstracts Service: Colorants and Dyes, Oct. 21, 1996.
Abstract No. 127846k, Chemical Abstracts Service: Colorants and Dyes, Oct. 13, 1994.
Abstract No. 168141c, Chemical Abstracts Service: Colorants and Dyes, Jan. 10, 1997.
Abstract No. 282145a, Chemical Abstracts Service: Colorants and Dyes, Jul. 11, 1991.
Abstract No. 349039w, Chemical Abstracts Service: Colorants and Dyes, Apr. 10, 1997.

Abstract No. 14995t, Chemical Abstracts Service: Colorants and Dyes, Apr. 16, 1997.

Abstract No. 245176b, Chemical Abstracts Service: Colorants and Dyes, Sep. 19, 1996.

Abstract No. 19534q, Chemical Abstracts Service: Colorants and Dyes, Jan. 19, 1996.

Abstract No. 234412n, Chemical Abstracts Service: Colorants and Dyes, Dec. 21, 1994.

Abstract No. 108910y, Chemical Abstracts Service: Colorants and Dyes, Jul. 17, 1991.

STN International® Caplus, Database, Accession No. 1975:516012; Alan K. Schein DE 2452870 (1975), abstract.

RN 123764-97-6, RN 125811-49-6, RN 125811-44-1, RN 103941-64-6, RN 65603-19-2, RN 138337-12-9.

Aida JP 63-316852 (1988).

PHASE CHANGE INK FORMULATIONS, COLORANT FORMULATIONS, AND METHODS OF FORMING COLORANTS

CROSS-REFERENCE TO RELATED APPLICATIONS

This application is a divisional application of U.S. patent application Ser. No. 09/772,617 (now U.S. Pat. No. 7,022,879), filed Jan. 30, 2001; which is in turn a divisional application of U.S. patent application Ser. No. 09/397,348 (now U.S. Pat. No. 6,235,094), filed on 15 Sep. 1999; which is in turn a continuation-in-part application of U.S. patent application Ser. No. 09/023,851 (now U.S. Pat. No. 6,028,138), filed on Feb. 13, 1998; which is in turn a continuation-in-part application of U.S. patent applications Ser. No. 08/672,815 (now U.S. Pat. No. 5,830,942), filed Jun. 28, 1996 and U.S. patent application Ser. No. 09/013,410 (now U.S. Pat. No. 5,994,453), filed Jan. 26, 1998.

BACKGROUND OF THE INVENTION

1. Field of the Invention

The invention relates to new colorant compositions, and to methods of forming and using such colorants. In particular applications, the invention pertains to phase change ink formulations.

2. Description of the Relevant Art

The present invention encompasses new colorant compounds, routes to their preparation, and methodology for incorporating such compounds into phase change inks. Phase change inks are compositions which are in a solid phase at ambient temperature, but which exist in a liquid phase at an elevated operating temperature of an ink jet printing device. At the jet operating temperature, droplets of liquid ink are ejected from the printing device. When the ink droplets contact the surface of a printing media, they solidify to form a printed pattern. Phase change ink methodology is described generally in U.S. Pat. Nos. 4,889,560; 5,372,852 and 5,827,918.

A definition which will be adopted in this disclosure and the claims that follow will be to utilize the term "colorant" to refer to modified dyes, chromophores and pigments which are suitable for inclusion in phase change inks. Another definition which will be adopted in this disclosure and the claims that follow will be to refer to a phase change ink composition as comprising a colorant and a carrier. The term "carrier" is to be understood to comprise all components of a phase change ink composition with the exception of the colorant. In phase change ink compositions comprising more than one colorant, the carrier will include everything except a particular colorant of interest, and can, therefore, comprise colorants other than that which is of interest.

A difficulty associated with phase change inks can be in solubilizing traditionally utilized dyes, chromophores and pigments. Many colored compounds useful in producing phase change inks for digital printing generally comprise polar functional groups, and accordingly are insoluble in the organic carrier of a phase change ink composition. The solubility of the colored compounds can be improved by increasing the hydrophobic character of the colored compounds. Accordingly, it is desirable to develop methods for increasing the hydrophobic character of existing chromophores, dyes and pigments to produce new colored compounds, as well as to develop new colorants with substantial hydrophobic character.

BRIEF SUMMARY OF THE INVENTION

In one aspect, the invention encompasses a compound having the formula:

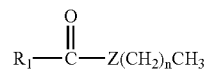

wherein $R_1$ comprises a chromophore that absorbs light from the visible wavelength range, and wherein n is an integer that is at least 12.

In another aspect, the invention encompasses a solid phase change ink composition. Such composition includes a phase change ink carrier and a colorant. The colorant comprises a chromophore that absorbs light from the visible wavelength range, and has the formula:

wherein n is an integer that is at least 12.

In yet another aspect, the invention encompasses a method of forming a colorant. A first compound having the formula,

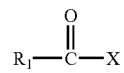

is reacted with a second compound having the formula $Z(CH_2)_nCH_3$, wherein n is an integer that is at least 12, to form a third compound having the formula,

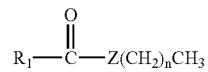

wherein the third compound comprises a chromophore that absorbs light from the visible wavelength range and is soluble in a phase change ink.

DESCRIPTION OF THE PREFERRED EMBODIMENTS

Figure 1:
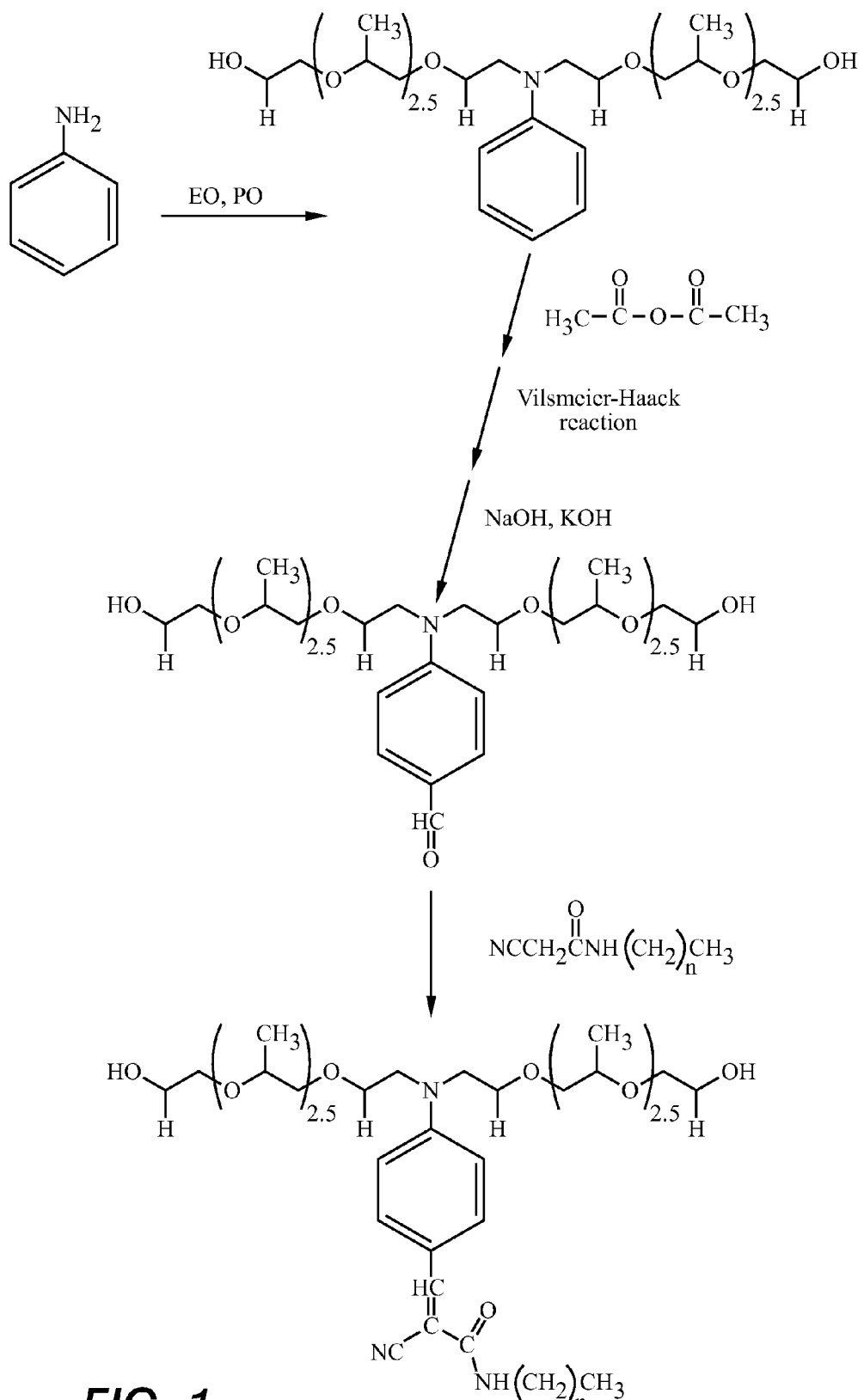
FIG. 1 shows a generalized reaction scheme comprising methodology of the present invention.

The invention comprises new colorants, as well as new phase change ink compositions comprising the colorants. The new colorants have a substantial amount of hydrophobic character. In one aspect, the hydrophobic character is imparted by incorporating at least one alkyl or alkoxylate chain that is at least 13 carbon units long into colorants of the present invention. In particular embodiments, the alkyl or alkoxylate chain is at least 20 carbon units long, and in other embodiments at least 40 carbon units long. It can be preferred that the number of carbon atoms in the alkyl or alkoxylate chain not exceed about 300, as such long carbon chains (if present in sufficient concentration) can increase a melting point of a phase change ink beyond a desired limit of about 170° C. Of course, if a colorant is provided to a sufficiently low concentration in a phase change ink such that carbon chains comprising greater than 300 carbon units do not adversely affect a melting point of the ink, the preferability of having less than 300 carbon units is diminished. Also, it is noted that eutectic mixtures comprising a colorant can lower a melting point of the colorant so that a melting point of the colorant can be less than or equal to 170° C. even if the colorant has chains with more than 300 carbon units. Consequently, it is noted that a melting point temperature of a phase change ink can be engineered even from colorants having melting points significantly different than that ultimately desired in the phase change ink.

A general formula for one class of colorant encompassed by the present invention is shown below as compound 1.

1

The group $R_1$ of compound 1 comprises a chromophore that absorbs light from the visible wavelength range (i.e., light having a wavelength of from about 400 nanometers to about 750 nanometers). The label n of compound 1 represents an integer that is at least 12. In preferred embodiments, n is at least 17. In further preferred embodiments (particularly where the colorant is provided in high concentration in a phase change ink, with high concentration being defined as a concentration greater than about 25% (by weight) of the ink), n is less than or equal to 299. The segment Z of compound 1 comprises one or more atoms; and comprises an atom selected from group IV of the periodic table (i.e., the group comprising carbon), group V of the periodic table (i.e., the group comprising nitrogen) or group VI of the periodic table (i.e., the group comprising oxygen and sulphur).

Although the compound 1 is shown in a linear form, it is to be understood that compound 1 can be comprised by a cyclic structure (i.e., compound 1 can be a portion of a cyclic structure), and that the carbonyl, $R_1$ and Z can be contained in a common ring of such cyclic structure. Compound 1A shows a dashed line to indicate the ring of a cyclic structure of compound 1.

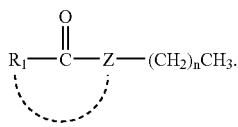

1A

In particular embodiments, the segment $Z(CH_2)_nCH_3$ of compound 1 is either group 2 (below) or group 3 (below).

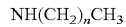  2.

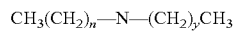  3.

In group 3, the label y is an integer that can be the same or different than n, and which is preferably greater than 12, although it can be zero. The amines (or generally a nucleophile) of groups 2 and 3 correspond to the component Z of compound 1.

The segment $R_1$ of compound 1 comprises carbon, and can comprise, for example, aryl moieties in color-yielding combinations. Exemplary aryl moieties are phenyl and naphthyl. The segment $R_1$ and the carbonyl of compound 1 can together comprise a chemical group selected from the group consisting of ester, lactone, amide, lactam and imide. Further, $R_1$ and the carbonyl of compound 1 can together comprise an auxochrome. The group $R_1$ can also comprise an auxochrome by itself by containing electron donating groups or electron withdrawing groups.

Further, the group $R_1$ of compound 1 preferably comprises a chromophore that absorbs light within the visible wavelength range such that compound 1 can be a suitable colorant for a phase change ink. Among the preferred chromophores for phase change inks are chromophores corresponding to cyan, magenta, yellow or black colors. The chromophore encompassed by the compound 1 can comprise, for example, methine, metal phthalocyanine, metal phthalocyanine, azamethine, azo, triphenylmethane, rhodamine, xanthene, indoaniline, pyridone, perylene, anthrapyridone and anthraquinone.

In an exemplary embodiment, compound 1 can have a formula corresponding to that of compound 4 (shown below).

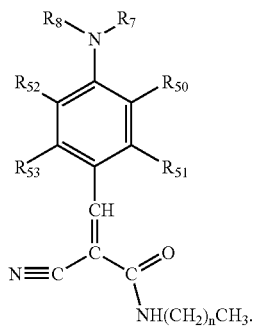

4

The components $R_{50}$, $R_{51}$, $R_{52}$, and $R_{53}$ of compound 4 can, for example, be selected from the group consisting of hydrogen, halogens, hydroxy groups, alkoxy groups, trifluoromethyl groups, and alkyl groups, and can be the same as one another or different than one another. The components $R_7$ and $R_8$ of compound 4 are selected from the group consisting of hydrogen and carbon-containing materials, and can be, for example, alkyl moieties, aryl moieties or hydrogen. Components $R_7$ and $R_8$ can be the same or different relative to one another, and can be comprised by a common ring. In particular embodiments, at least one of the components $R_7$ and $R_8$ of compound 4 can comprise a chain having the formula of material 5.

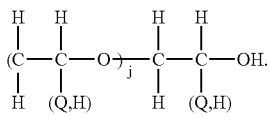

In material 5, j is an integer of from 0 to about 300 (preferably from 0 to 100, and more preferably from 1 to 10), and the representation of "(Q, H)" indicates that either a substituent Q or a hydrogen can be in the shown positions. Substituent Q represents either an alkyl group or an aryl group, and can vary amongst different alkyl and aryl groups within either or both of components $R_7$ and $R_8$. In particular embodiments, Q is $CH_3$ throughout both of $R_7$ and $R_8$.

A compound corresponding to compound 4, and having $R_7$ and $R_8$ corresponding to the formula of material 5, can be formed according to the reaction scheme shown in FIG. 1. Specifically, aniline is alkoxylated to yield anilined 252 (shorthand for aniline with 2 moles of ethylene oxide (EO), 5 moles of propylene oxide (PO) and 2 moles of EO to yield a block co-polymer). The aniline 252 of FIG. 1 corresponds to a combination of aniline and a pair of polymers encompassed by material 5, with the polymer encompassed by material 5 having the formula shown below as 5A (i.e., a 1:2.5:1 structure).

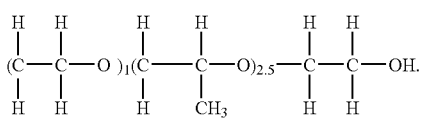

The 2.5 of material 5A indicates that on average there are 2.5 of the $CH_2CH(CH_3)O$ units in a chain. Of course, in any given chain, the actual number of such units will be an integer amount (typically 2 or 3).

After formation of the aniline 252 in the FIG. 1 reaction process, the aniline 252 is acetylated. After the acetylation, a resulting aniline 252 diacetate is converted to an aldehyde by a Vilsmeier-Haack reaction utilizing phosphorus oxychloride and N,N-dimethylformamide (DMF). Basic hydrolysis of the acetate protecting groups is accomplished with warm dilute sodium hydroxide containing a small percentage of potassium hydroxide. The benzaldehyde derivative containing the free hydroxyl groups on the alkoxylate chain is neutralized, phased by warming to above the cloud point, and allowed to stand and separate. The salt layer is removed and the resulting aldehyde layer is reduced in vacuo to yield the anhydrous precursor of a chromophore. The aldehyde is then condensed with a cyanoacetate derivative to form the resulting exemplary colorant of the present invention.

Other epoxides can be utilized instead of, or in addition to, the EO and PO epoxides discussed above. For instance, butylene oxide (BO) and/or styrene oxide (SO) can also be utilized.

The reaction chemistry shown in FIG. 1 is an example of a condensation reaction encompassed by the present invention. A more general description of condensation reactions of the present invention is a follows. First, a starting material 10 (shown below, and referred to hereafter as "compound 10") is provided.

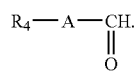

The segment A of compound 10 is an aromatic ring, and the group $R_4$ of compound 10 comprises one or both of carbon and hydrogen. Compound 10 is reacted with a cyanoacetate derivative 11 having the formula shown below.

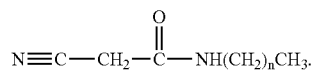

The label "n" of cyanoacetate derivative 11 represents an integer, and is preferably at least 12.

Condensation of aldehyde compound 10 with cyanoacetate derivative 11 forms a product having formula 12.

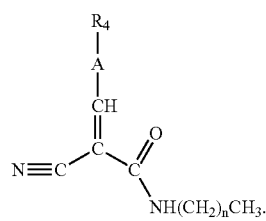

Compound 12 is a methine colorant, and an exemplary compound encompassed by the present invention. In a particular embodiment of the invention, compound 11 comprises a stearyl amide of cyanoacetic acid, and compound 10 comprises N,N-dialkyl amino benzaldehyde. Condensation of compounds 10 and 11 yields a compound 12 corresponding to a methine yellow colorant.

Methine dyes and pigments represent an important class of chromogen in virtually every area requiring a yellow to cyan hue. Numerous derivatives have been made and have been used to make many types of dyes (e.g., dispersed, acid, reactive, etc.). Some shortcomings of prior art methine dyes in hot melt wax systems (i.e., phase change ink systems) are due to solubility and blooming problems. These arise from the relatively small and compact structure of prior art methine dyes. Because of their structures, aggregation of dye moieties readily takes place. Such aggregation can lead to solubility problems (aggregated molecules can combine and form precipitates which can adversely affect printhead performance), as well as to blooming if the unaggregated molecules migrate to the surface of a printed image.

An advantage of the present invention is that it encompasses synthetic methods which can be utilized to create methine colorants while overcoming the manufacturing and preparation disadvantages associated with prior art methine dye preparation (i.e., the use of hazardous and/or volatile solvents and elaborate purification procedures). Specifically, reactions of the present invention are preferably run without traditional volatile organic solvents. Instead, the reactions are preferably run at temperatures that allow each component, each intermediate, and each final product to be molten. Accordingly, the reaction mixture functions as its own solvent, and no additional solvents are needed. Suitably high temperatures are employed to keep the reaction molten during its duration, as well as to allow water and/or low molecular weight alcohols to be removed. Example 1 describes an exemplary colorant preparation procedure encompassed by the present invention. The colorant obtained from the process of Example 1 has a viscosity similar to the desired viscosity of a final ink, and could, accordingly, be utilized as ink directly, rather than being utilized in combination with a carrier. However, the colorant was tested for suitability in phase change ink applications by combining the colorant with a phase change ink carrier solution. Specifically, the colorant was combined with an ink base, filtered and printed (see Example 2 for preparation of the ink base, and Example 3 for combination of the colorant and ink base).

The method described above with reference to compounds 10-12 utilized a cyanoacetate derivative having an alkyl chain with at least 13 carbon atoms incorporated therein (compound 11). Another method encompassed by the present invention is to utilize a cyanoacetate derivative which does not have the alkyl chain with at least 13 carbon atoms already incorporated therein, but which can be subsequently reacted to incorporate an alkyl group having at least 13 carbon atoms. For instance, the compound 10 which was discussed above can be reacted with a second compound 13, to form a third compound 14.

13

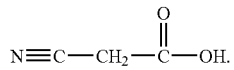

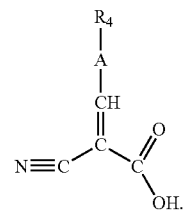

14

Compound 14 can be subsequently reacted with $NH_2(CH_2)_nCH_3$ to form the compound 12 that was discussed above. While the invention is not limited by the process order for introducing the alkyl group feature, a specific advantage of the invention can be to prepare a new colorant through solventless transformation in a molten state.

An exemplary material for compound 10 is shown below as compound 15.

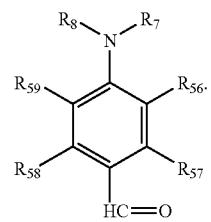

15

The components $R_{56}$, $R_{57}$, $R_{59}$, and $R_{59}$ of compound 10 can, for example, be selected from the group consisting of hydrogen, halogens, hydroxy groups, alkoxy groups, trifluoromethyl groups, and alkyl groups, and can be the same as one another or different than one another. The components $R_7$ and $R_8$ of compound 15 are selected from the group consisting of hydrogen and carbon-containing materials, and can be, for example, alkyl moieties, aryl moieties or hydrogen. Components $R_7$ and $R_8$ can be the same or different relative to one another, and can be comprised by a common ring. In particular embodiments, at least one of $R_7$ and $R_1$ comprises a chain having the formula of material 5, wherein j is an integer from 0 to about 300, and wherein Q is hydrogen or $CH_3$, and can vary between hydrogen and $CH_3$ within the chain to yield block co-polymers.

Another composition which can be formed by methodology similar to that shown in FIG. 1 is compound 6 (below). An exemplary material encompassed by the formula of compound 6 can be formed by the methodology shown in FIG. 2.

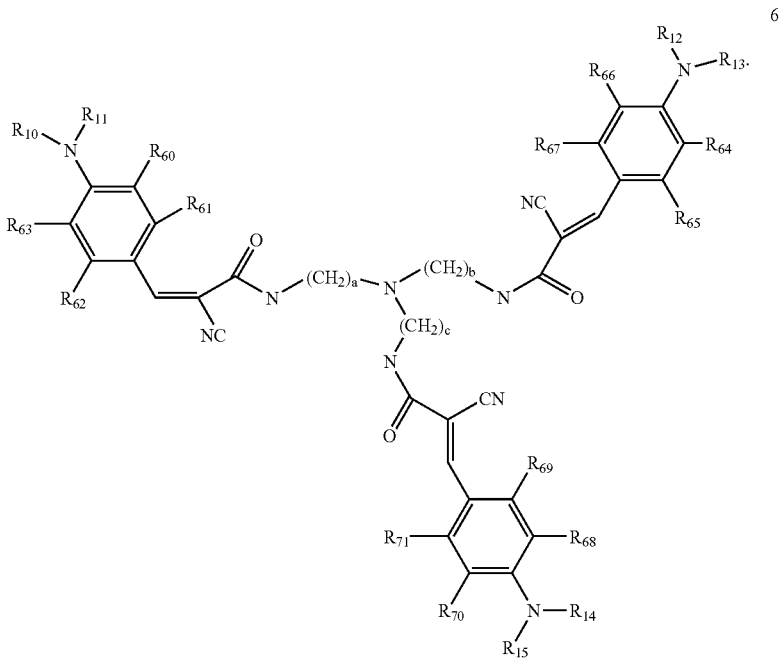

The components $R_{60}$, $R_{61}$, $R_{62}$, $R_{63}$, $R_{64}$, $R_{65}$, $R_{66}$, $R_{67}$, $R_{68}$, $R_{69}$, $R_{70}$, and $R_{71}$ of compound 6 can, for example, be selected from the group consisting of hydrogen, halogens, hydroxy groups, alkoxy groups, trifluoromethyl groups, and alkyl groups, and can be the same as one another or different than one another. The components $R_{10}$, $R_{11}$, $R_{12}$, $R_{13}$, $R_{14}$ and $R_{15}$ of compound 6 are selected from the group consisting of hydrogen and carbon-containing materials, and can be, for example, alkyl moieties, aryl moieties or hydrogen. Components $R_{10}$, $R_{11}$, $R_{12}$, $R_{13}$, $R_{14}$ and $R_{15}$ can be the same or different relative to one another. In particular embodiments, at least one of the groups $R_{10}$, $R_{11}$, $R_{12}$, $R_{13}$, $R_{14}$ and $R_{15}$ can comprise a chain having the formula of material 5. The labels "a", "b", and "c" of compound 6 are integers of from 1 to 300, and preferably from 1 to 100, and more preferably of from 1 to 10, and can be the same or different from one another.

Figure 2:
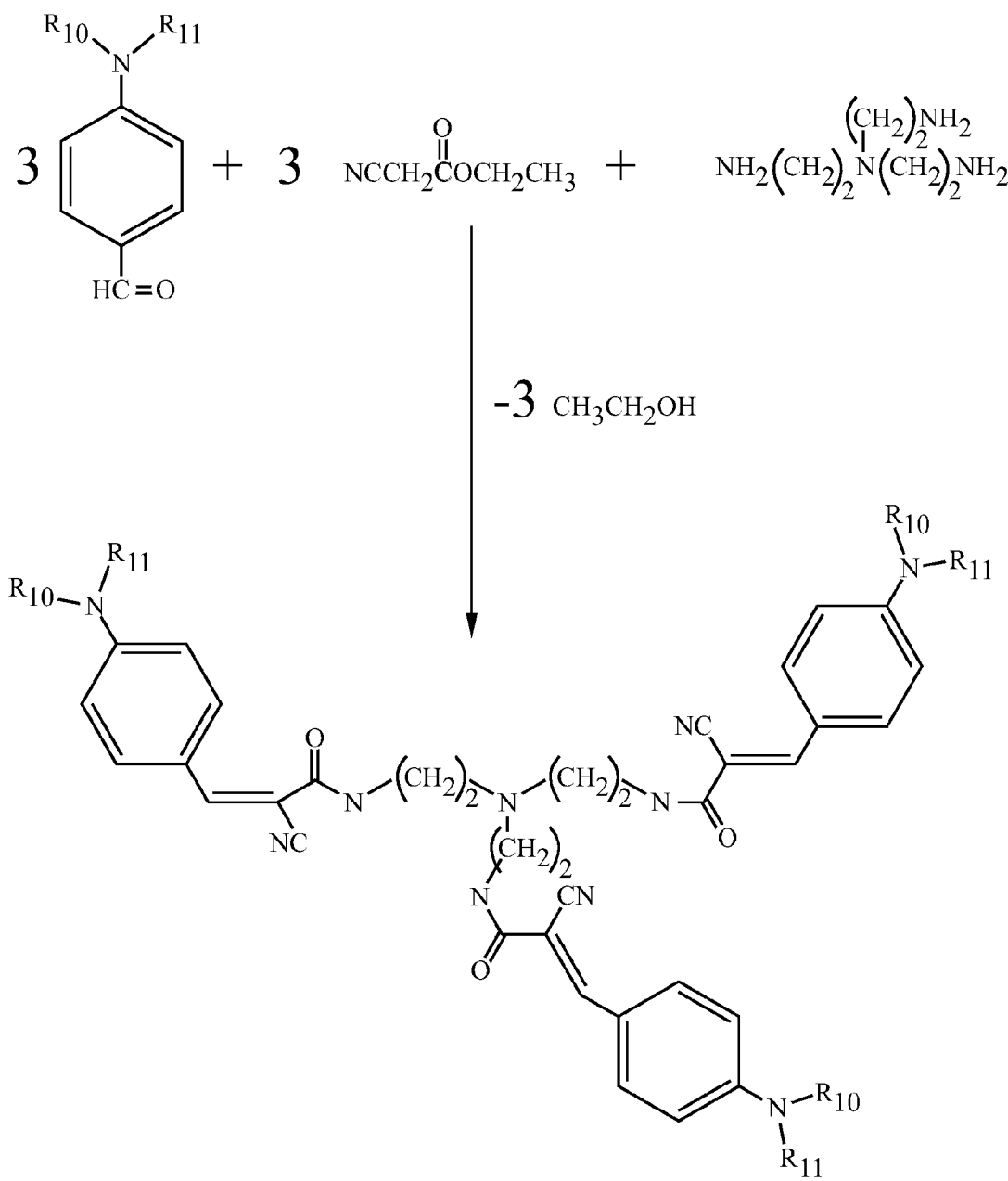
FIG. 2 shows a generalized reaction scheme of a net overall reaction comprising methodology of the present invention.

The FIG. 2 reaction scheme shows a method of forming an exemplary compound 6 having "a", "b" and "c" equal to 2, and $R_{60}$-$R_{71}$ as hydrogen. The resulting compound has a significant amount of hydrophobic character due to the three carbon tethers (which are linked in the common starting material tris-triethylamino amine, and joined with a common nitrogen molecule). (The term "tether" is used herein to refer to an organic linkage between two components.) Compound 6 is an exemplary compound of the present invention. Materials other than compound 6 can be formed by substituting other molecules for the tris-triethylamino amine of FIG. 2. Such other molecules can comprise longer carbon chains than tris-triethylamino amine, and more than the three tethers of tris-triethylamino amine. Also, the nitrogen nucleophiles of the tris-triethylamino amine can be replaced with other nucleophiles (such as, for example, oxygen or sulfur), such that one or more of the amide linkages shown in compound 6 is replaced by a different type of linkage (such as, for example, an ester or a thioester). Additionally, the central amine of triethylamino amine can be replaced with a different atom, such as, for example carbon. A starting material that can be substituted for the tris-triethylamino amine, and which comprises a central carbon atom instead of the central nitrogen of tris-triethylamino amine, is a T-SERIES JEFFAMINE™ (available from Huntsman Chemical of Austin, Tex.). Another exemplary starting material which could be substituted for tris-triethylamino amine is polyethylene imine, TETRONIC™ (available from BASF Corporation of Parsippany, N.J.). Yet another exemplary starting material is a material comprising a combination of two or more of T-SERIES JEFFAMINE™, polyethylene imine, and tris-triethylamino amine.

In light of the above-discussed substitutions for the tris-triethylamino amine utilized during formation of compound 6, it will be recognized that compound 6 is but one representative of a class of compounds encompassed by the present invention. Such class comprises at least two segments having the formula 20 shown below, with the at least two segments being joined through a common central atom or multi-atom structure. If the at least two segments are joined through a common atom, such atom can be either carbon, sulfur, phosphorus or nitrogen. In segment 20, $R_{20}$ and $R_{21}$, comprise one or both of carbon and hydrogen; $Z_5$ comprises carbon, nitrogen, oxygen or sulfur; the components $R_{73}$, $R_{74}$, $R_{75}$, and $R_{76}$ can, for example, be selected from the group consisting of hydrogen, halogens, hydroxy groups, alkoxy groups, trifluoromethyl groups, and alkyl groups, and can be the same as one another or different than one another; and b is an integer of from 1 to 300, and preferably of from 2 to 20. Another way of describing a compound having at least two segments 20 is shown as compound 21 (below), wherein G corresponds to a common central atom or multi-atom structure that joins the segments, wherein $Z_5$, b, $R_{20}$ and $R_{21}$ can be the same or different at different segments within the compound, and wherein d is at least 2. In particular embodiments, a compound of the present invention has at least three segments having the formula 20, and accordingly, d of compound 21 is an integer that is at least 3.

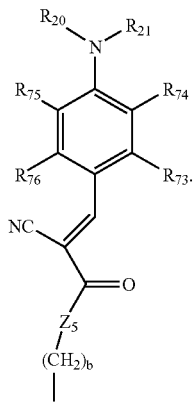

20

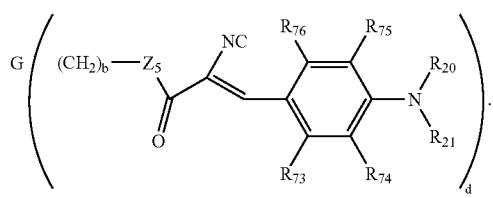

21

It is noted that compound 6 can be reacted with organic acids, mineral acids, or combinations of organic and mineral acids, to protonate one or more of the amines and accordingly form ion pairs comprising the protonated compounds and negative counterions. Exemplary acids are stearic acid, hydrochloric acid, sulfuric acid, and dodecyl benzene sulfonic acid. The ion pairs formed from compound 6 and the acids can constitute colorants having high molecular weights and desired non-blooming, non-migrating properties in phase change inks. This aspect of the invention can provide a route to materials which exhibit solubilized pigment behavior.

The above-described materials (materials 1-6, 10-15, 20 and 21) can be utilized as colorants in phase change inks. Accordingly, the materials can be combined with a phase change ink carrier to form a phase change ink composition. Preferably, the materials will be present in the ink composition to a concentration of from about 0.5% to about 60%, and most preferably between 5% and 30%. In the particular cases wherein the colorants have appropriate viscosity and melting temperature to provide printable properties at a printhead operating temperature, a phase change ink can consist essentially of the colorant (i.e., the phase change ink will be essentially pure colorant, and accordingly have no carrier).

Figure 3:
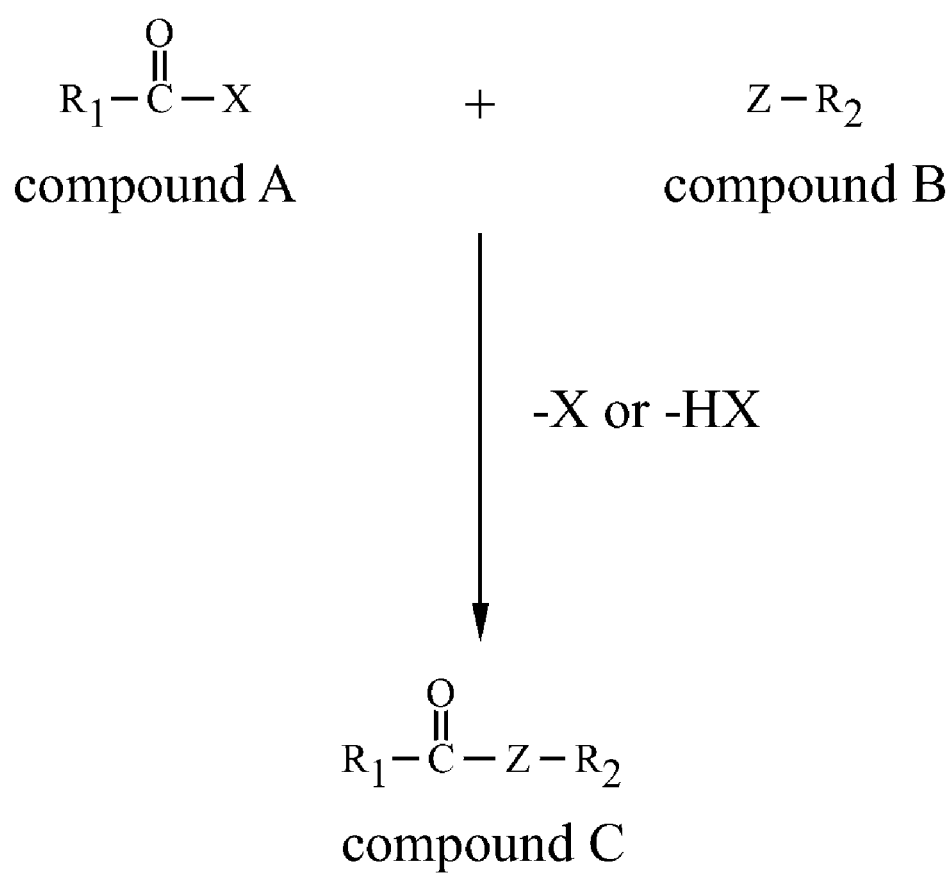
FIG. 3 shows yet another generalized reaction scheme of a net overall reaction comprising methodology of the present invention.

The methods described above with reference to FIGS. 1 and 2 are exemplary methods for forming compounds encompassed by the present invention. Another exemplary method is shown in FIG. 3. Specifically, FIG. 3 shows that a first compound "A" (which has a carbonyl attached to a leaving group X) is reacted with a second compound "B" (which has a component Z bonded to a carbon-containing group $R_2$) to form a third compound "C". In particular aspects of the invention, the group $R_2$ can comprise an alkyl chain having at least 13 carbon atoms. In other embodiments, the group $R_2$ can comprise a component suitable for subsequent bonding with an alkyl group having at least 13 carbon atoms. The reaction effectively substitutes group X with the group $ZR_2$. The group X can comprise, for example, $O(CH_2)_mCH_3$, with m being an integer of from 0 to 10. Preferably, m is an integer of from 0 to 2. The component Z can comprise, for example, a nucleophile, such as oxygen, sulphur or nitrogen. In particular embodiments of the invention, the material $Z-R_2$ comprises either of compounds 7 or 8, with n an y being integers which are preferably at least 12.

7

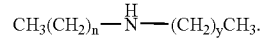

8

In a further particular embodiment, compound "A" of FIG. 3 can comprise the carbocation shown below as compound 9.

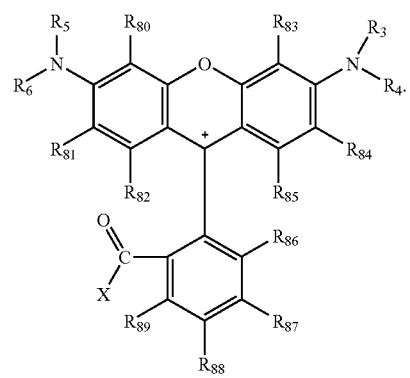

9

The components $R_{80}$, $R_{81}$, $R_{82}$, $R_{83}$, $R_{84}$, $R_{85}$, $R_{86}$, $R_{87}$, $R_{88}$, and $R_{89}$ of compound 9 can, for example, be selected from the group consisting of hydrogen, halogens, hydroxy groups, alkoxy groups, trifluoromethyl groups, and alkyl groups, and can be the same as one another or different than one another. The components $R_3$, $R_4$, $R_5$ and $R_6$ of compound 9 can be selected from the group consisting of hydrogen and carbon-containing materials, and can be, for example, alkyl moieties, aryl moieties or hydrogen. Further, the groups $R_3$, $R_4$, $R_5$ and $R_6$ of compound 9 can be the same or different than one another.

The reaction of FIG. 3 can comprise, for example, an alkylamino-de-alkoxylation reaction which is utilized to add a carbon chain (such as, for example, a stearyl group) to a chromophore. The addition of a suitable carbon chain can form a colorant having improved properties for utilization in a phase change ink relative to the starting chromophore. For instance, the addition of a suitable carbon chain can form a colorant having increased molecular weight, enhanced solubility in an ink base (decreasing the blooming tendency) and decreased tendency to migrate, relative to the starting chromophore.

An exemplary chromophore which can be treated by alkylamino-de-alkoxylation is INTRATHERM YELLOW P-346™, available from Crompton and Knowles. INTRATHERM YELLOW P-346™ provides a bright yellow color when formulated into phase change ink bases. In addition, the dye shows good lightfastness and good thermal stability compared to conventional yellow colorants. Unfortunately, at dye loads much above 1% the dye has a tendency to "bloom" to the surface of a test print. In addition, the dye tends to migrate under tape and lamination media. An alkylamino-de-alkoxylation transformation encompassed by the present invention can improve the performance of INTRATHERM YELLOW P-346™ in phase change inks. For instance, Example 4 (below), together with the data following Example 4, shows that modification of INTRATHERM YELLOW P-346™ in accordance with the present invention can enhance the image stability of printed phase change test images relative to unmodified INTRATHERM YELLOW P-346™. Further, although the example modification is relative to INTRATHERM YELLOW P-346™, the procedure of the present invention can be readily utilized on a large number of chromophores to enhance their solubility and migration fastness in phase change inks, and accordingly, the commercialization potential of such chromophores is significantly increased. This feature of the invention is also applicable for the preparation of solvent soluble colorants from dyes typically insoluble in organic carriers.

Exemplary embodiments of the present invention are described in the Examples below. It is to be understood, however, that the Examples are provided for illustration purposes only. The invention is to be limited only by the claims which follow, and not by the chemistry shown in the following Examples except to the extent that such chemistry is expressly recited in the following claims.

EXAMPLE 1

Octadecyl amine[1] (about 135.9 grams (0.505 moles)) was carefully heated in a one-liter four-neck resin kettle equipped with a Trubore stirrer, thermocouple-temperature controller, $N_2$ atmosphere, and vacuum adapter to about 80° C., at which time it became molten and agitation was begun. Once the octadecyl amine was molten, about 50.0 grams (0.505 moles) of methyl cyanoacetate[2] was slowly added. When the addition was complete, the temperature was held at about 90° C. for approximately 45 minutes and then slowly raised to about 150° C. After about one hour at about 150° C., the $N_2$ atmosphere was removed and a vacuum was applied. After about one hour, the vacuum was removed, the $N_2$ atmosphere was re-established, and the temperature was lowered to about 135° C. When the temperature reached about 135° C., about 71.5 grams (0.480 moles) of dimethylaminobenzaldehyde[3] were added and heated, under $N_2$, for about one hour. The $N_2$ atmosphere was then removed, the temperature was increased to about 150° C., and a vacuum was applied. After about one hour, the vacuum was removed and the reaction product was poured into aluminum pans and allowed to cool and solidify. The final product was a yellow solid at room temperature. A sample of the final product was dissolved in toluene, and was determined to have a spectral strength of about 69,560 (milliliters*Absorbance Units/gram) at a lambda$_{max}$ of 407 nm. The spectral strength was measured using a Perkin Elmer Lambda 2S UV/VIS spectrophotometer.

[1] ARMEEN 18D FLK—Octadecyl amine available from AKZO NOBEL Chemicals Inc. of McCook, Ill.
[2] Methyl cyanoacetate—available from Aldrich Chemicals of Milwaukee, Wis.
[3] Dimethylaminobenzaldehyde—available from Aldrich Chemicals of Milwaukee, Wis.

EXAMPLE 2

About 600.0 grams of stearyl stearamide[4], about 432.0 grams (1.674 moles) of octylphenol ethoxylate[5], about 252.0 grams (0.696 moles) of hydroabietyl alcohol[6], and about 273.0 grams (0.52) moles of C-32 linear alcohol[7] were mixed in a 3 L four-neck resin kettle equipped with a Trubore stirrer, $N_2$ atmosphere, addition funnel (200 mL), and thermocouple-temperature controller. This mixture was heated to 125° C. and agitation begun when all components were molten (at approximately 100° C.). To the mixture, and about 334.2 grams (1.505 moles) of isophorone diisocyanate[8] was added over approximately five minutes through the addition funnel. About 0.66 grams of dibutyltindilaurate[9] was added and the reaction mixture heated to about 150° C. After about two hours at about 150° C., additional amounts of about 45.0 grams (0.174 moles) of octylphenol ethoxylate, about 45.0 grams (0.124 moles) of hydroabietyl alcohol, about 45.0 grams (0.086 moles) of C-32 linear alcohol, and about 0.05 grams of dibutyltindilaurate were added and the reaction mixture maintained at about 150° C. for about two hours. A Fourier transform infrared spectrum (FT-IR spectrum) of the reaction product was obtained to insure that all of the isocyanate functionality was consumed. The absence (disappearance) of a peak at ~2285 cm$^{-1}$ (NCO) and the appearance (or increase in magnitude) of peaks at ~1740-1680 cm$^{-1}$ and ~1540-1530 cm$^{-1}$ corresponding to urethane frequencies were used to confirm this. The final mixed urethane product was then poured into aluminum molds and allowed to cool and harden. The resulting product was a solid at room temperature and characterized by a viscosity of about 14.92 cPs as measured by a Ferranti-Shirley cone-plate viscometer at about 140° C.

[4] S-180—stearyl stearamide available from Witco Corp., Greenwich, Conn.
[5] IGEPAL CA-210—octylphenol ethoxylate, available from Rhone-Poulenc Co., Cranbury, N.J.
[6] Abitol E—hydroabietyl alcohol available from Hercules Inc. of Wilmington, Del.
[7] UNILIN 425—C-32 linear alcohol available from Baker petrolite of tulsa, Okla.
[8] Desmodur I—isophorone diisoyanate available from Bayer corp. of Pittsburgh, Pa.
[9] FASCAT 4202—dibutyltindilaurate available from Elf atochem North America Inc. of Philadelphia, Pa.

EXAMPLE 3

About 345.0 grams of the material from Example 2, about 125.0 grams of Lawter SA-3850 (Lawter International, Inc. or Northbrook, Ill.), and about 10.0 grams of the yellow colorant from Example 1 were combined in a one-liter stainless steel beaker. The materials were melted together at a temperature of about 125° C. in an oven, then blended by stirring in a temperature controlled mantle at about 125° C. for about one-half hour to form a yellow ink. The yellow ink was filtered through a heated Mott apparatus (available from Mott Metallurgical) using a 2 micron filter and a pressure of about 15 psi. The filtered phase change ink was poured into molds and allowed to solidify to form ink sticks. The final ink product had a viscosity of about 11.44 cPs as measured by a Ferranti-Shirley cone-plate viscometer at about 140° C. The product had a spectral strength of 1400 (milliliters*Absorbance Units/gram) at a lambda$_{max}$ of 407 nm when dissolved in toluene. The spectral strength was measured using a Perkin Elmer Lambda 2S UV/VIS spectrophotometer.

The ink was tested in a Tektronix PHASER™ 340 printer (which uses an offset transfer printing system), and was found to provide images of good color, print quality and durability.

EXAMPLE 4

A 100 mL one-neck flask was equipped with a magnet and placed in a silicone oil bath on a hot plate/magnetic stirrer. The flask was equipped with a vacuum adapter and configured to be filled with an $N_2$ atmosphere. About 10.0 grams of stearyl amine[10] and about 12.5 grams INTRATHERM YELLOW P346™[11] were mixed in the flask. The mixture was heated to about 95° C. in an $N_2$ atmosphere, at which time it became molten and agitation was begun. After about 0.5 hours at about 95° C., the temperature was increased to about 105° C. and held for approximately four hours. Bubbles were observed evolving from the reaction mixture for several hours. The temperature was then increased to about 110° C. and held for about six hours. The $N_2$ addition was then stopped, a vacuum was introduced to the reaction vessel, and the temperature was maintained at about 110° C. After about 30 minutes, the vacuum was removed, $N_2$ reintroduced, about 80 mL of toluene was added, and the reaction mixture allowed to cool to room temperature with stirring.

[10] ARMEEN 18D FLK—Octadecyl amine available from AKZO NOBEL Chemicals Inc. of McCook, Ill.
[11] INTRATHERM YELLOW P-346—Disperse Yellow 238 available from Crompton and Knowles Colors, Inc., Charlotte, N.C.

The reaction product in toluene was then poured into a 600 mL coarse frit Buchner funnel containing a toluene slurry of silica gel[12] and attached to a 1-liter vacuum flask. About 500 mL of toluene was eluted through the silica gel and subsequently removed via rotary evaporation. This toluene elution step was repeated two additional times, and a final time with acetone. A total of four 500 mL fractions were collected and concentrated. Thin layer chromatography (TLC) on reversed phase plates of the four fractions was performed (using methanol as an eluent) and simultaneously compared with the starting dye. The third fraction showed the highest percentage of the desired, purified product. The purified reaction product (referred to hereafter as stearyl-modified INTRATHERM YELLOW P-346™) was a deep orange wax. The spectral strength of the purified product was determined in toluene to be 33,400 (milliliters*Absorbance Units/gram) at 414 nm. The peak width at half height was determined to be 110 nm.

[12] Silica Gel—70-230 mesh column chromatography grade available from Aldrich Chemical Co., Milwaukee, Wis.

Image Stability Characterization of the
Stearyl-Modified INTRATHERM YELLOW
P-346™

Two inks were prepared utilizing a common phase change ink carrier. The only difference between the two inks was that one of the inks used INTRATHERM YELLOW P-346™ as a colorant, and the other ink used the stearyl-modified INTRATHERM YELLOW P-346™ of Example 4 as a colorant. The dye proportions in the two inks were adjusted to normalize the spectral strength. The two inks were printed on a PHASER™ 600 printer and the relative performance of the inks was compared by several test methods. Results of these tests are tabulated below.

A. Color Print Test

The ink comprising stearyl-modified INTRATHERM YELLOW P-346™ as a colorant gave a slightly reddish yellow solid fill of high chromaticity. The color space was determined and is listed below in Table 1.

TABLE 1

| COLOR | L* | a* | b* |
|---|---|---|---|
| Cyan | 50.66 | −19.91 | −42.91 |
| Magenta | 49.48 | 73.53 | −20.17 |
| Yellow | 82.00 | 3.12 | 94.73 |
| Black | 24.12 | 0.81 | −0.44 |
| Red | 46.51 | 58.15 | 39.39 |
| Green | −38.91 | 24.47 | 11.2 |
| Blue | 26.44 | 28.97 | −44.38 |

B. Diffusion

The extent of dye diffusion was determined by using the CIELAB color-difference formula[13] for measurements of the same test panel before and after aging 72 hours in a 45° C. oven. The resulting color difference values (ΔE) are summarized in Table 2, which lists diffusion observed for two types of prints: unlaminated and laminated. Test panels containing small amounts of the diffusing color surrounded by large amounts of a second color have been observed to be most sensitive to dye diffusion. The proportion of the primary process colors in each test panel is shown in column 1 of Table 2. Data obtained utilizing commercially available INTRATHERM YELLOW P-346™ is listed under the category "Unmodified" in Table 2, and data obtained from the stearyl-modified INTRATHERM YELLOW P-346™ of Example 4 is listed under the category "Modified" in Table 2. The data in Table 2 show that the stearyl-modified INTRATHERM YELLOW P-346™ has about a 56% improvement when unlaminated, and about a 28% improvement when laminated relative to test panels containing unmodified INTRATHERM YELLOW P-346™.

[13] ASTM Method D 2244-89Standard Test Method for Calculation of Color Differences from Instrumentally Measured Color Coordinates.

TABLE 2

DIFFUSION TEST RESULTS
(ΔE, relative to initial color measurement)

| | Test Panel Composition | | | |
|---|---|---|---|---|
| | Unlaminated | | Laminated | |
| C/M/Y | Unmodified | Modified | Unmodified | Modified |
| 20/0/0 | 0.3 | 0.1 | n/a* | 0.3 |
| 20/100/0 | 1.8 | 0.8 | 2.6 | 2.9 |
| 20/0/100 | 1.6 | 1.6 | 1.6 | 1.4 |
| 100/20/0 | 5.4 | 5.7 | n/a* | 3.0 |
| 0/20/0 | 1.5 | 1.0 | 4.1 | 2.5 |
| 0/20/100 | 6.4 | 3.8 | 3.4 | 2.1 |
| 100/0/20 | 19.5 | 10.0 | n/a* | 14.3 |
| 0/100/20 | 14.3 | 8.5 | 16.2 | 11.7 |
| 0/0/20 | 2.7 | 0.5 | 24.9 | 18.3 |

*Means not available

C. Blooming

Blooming was tested by placing a printed solid fill image in a 60° C. oven for seven days. Prior to placement in the oven, the bottom section of the image was impressed with fingerprint oil. In addition, a strip of transparent tape was placed across the lower margin. Blooming could be observed in the sample comprising commercially available (i.e., unmodified) INTRATHERM YELLOW P-346™ after seven days, whereas the sample comprising stearyl-modified INTRATHERM YELLOW P-346™ did not exhibit significant blooming after the same period of time. In addition, a white facial tissue could be gently wiped across the sample comprising unmodified INTRATHERM YELLOW P-346™. This was not observed when performed with the sample comprising stearyl-modified INTRATHERM YELLOW P-346™.

D. Carryover of Sublimation onto Facing Sheet

The samples utilized for the blooming test (described above) were also utilized for testing carryover of sublimation onto a facing sheet. An unprinted sheet was provided over and in facing relation to the samples. Examination of the facing sheet revealed a noticeable migration of yellow dye from the sample comprising unmodified INTRATHERM YELLOW P-346™ after seven days at 60° C., and revealed no migration of yellow dye from the sample comprising stearyl-modified INTRATHERM YELLOW P-346™.

E. Tape Diffusion

Printed samples comprising stearyl-modified INTRATHERM YELLOW P-346™ were compared to printed samples comprising unmodified INTRATHERM YELLOW P-346™ for diffusion under transparent tape. Such comparison showed that the samples comprising stearyl-modified INTRATHERM YELLOW P-346™ had about a 50% improvement relative to the samples comprising stearyl-modified INTRATHERM YELLOW P-346™ (i.e., less colorant migration), as determined by visual inspection.

The invention claimed is:

1. A compound having the formula:

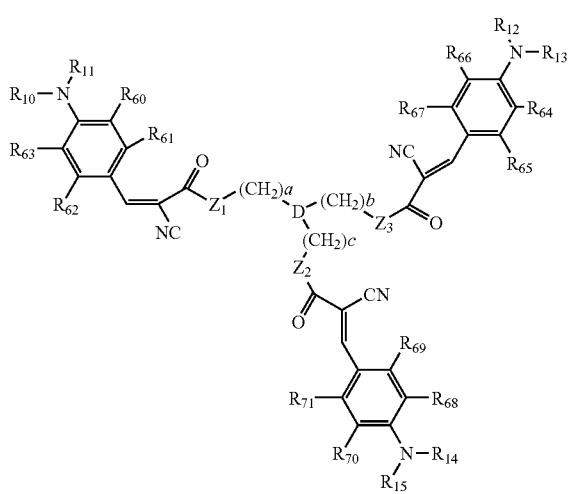

wherein $R_{60}$, $R_{61}$, $R_{62}$, $R_{63}$, $R_{64}$, $R_{65}$, $R_{66}$, $R_{67}$, $R_{68}$, $R_{69}$, $R_{70}$, and $R_{71}$ are selected from the group consisting of hydrogen, halogens, hydroxy groups, alkoxy groups, trifluoromethyl groups, and alkyl groups, and can be the same as one another or different from one another, wherein D is nitrogen in a cationic form, wherein $R_{10}$, $R_{11}$, $R_{12}$, $R_{13}$, $R_{14}$, and $R_{15}$ are selected from the group consisting of hydrogen, alkyl moieties, aryl moieties of the formula

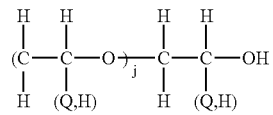

wherein j is an integer from 0 to about 300, wherein the representation of "(Q,H)" indicates that either a group Q or a hydrogen can be in the shown positions, wherein the group Q is either an alkyl group or an aryl group, and wherein Q can vary amongst different alkyl and aryl groups within the chain, and can be the same as one another or different from one another, wherein $Z_1$, $Z_2$, and $Z_3$ are each NH, and wherein a, b, and c can be the same as one another or defferent from one another one another and are integers that are at least 1.

2. A compound according to claim 1 wherein $R_{60}$, $R_{61}$, $R_{62}$, $R_{63}$, $R_{64}$, $R_{65}$, $R_{66}$, $R_{67}$, $R_{68}$, $R_{69}$, $R_{70}$, and $R_{71}$ are hydrogen.

3. A compound according to claim 1 wherein at least one of $R_{10}$, $R_{11}$, $R_{12}$, $R_{13}$, $R_{14}$, and $R_{15}$ is a chain having the formula

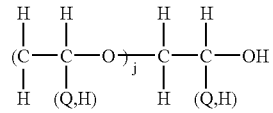

wherein j is an integer from 0 to about 300, wherein the representation of "(Q,H)" indicates that either a group Q or a hydrogen can be in the shown positions, wherein the group Q is either an alkyl group or an aryl group, and wherein Q can vary amongst different alkyl and aryl groups within the chain.

4. A compound according to claim 1 wherein each of $R_{10}$, $R_{11}$, $R_{12}$, $R_{13}$, $R_{14}$, and $R_{15}$ is a chain having the formula

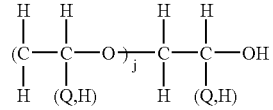

wherein j is an integer from 0 to about 300, wherein the representation of "(Q,H)" indicates that either a group Q or a hydrogen can be in the shown positions, wherein the group Q is either an alkyl group or an aryl group, and wherein Q can vary amongst different alkyl and aryl groups within the chain.

5. A compound of three segments of the formula shown below joined to one another though a nitrogen atom:

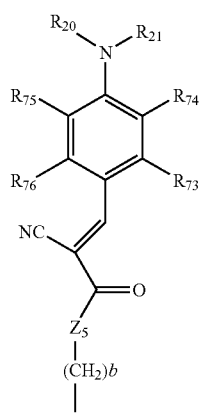

wherein $R_{73}$, $R_{74}$, $R_{75}$, and $R_{76}$ are selected from the group consisting of hydrogen, halogens, hydroxy groups, alkoxy groups, trifluoromethyl groups, and alkyl groups, and can be the same as one another or different from one another, wherein $R_{20}$ and $R_{21}$ are selected from the group consisting of hydrogen, alkyl moieties, aryl moieties, chains of the formula

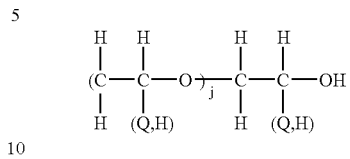

wherein j is an integer from 0 to about 300, wherein the representation of "(Q,H)" indicates that either a group Q or a hydrogen can be in the shown positions, wherein the group Q is either an alkyl group or an aryl group, and wherein Q can vary amongst different alkyl and aryl groups within the chain, and can be the same as one another or different from one another, wherein $Z_5$ is NH, wherein b is an integer that is at least 1, the integer b being the same or different amongst the different segments, and the groups $R_{20}$ and $R_{21}$ being the same or different amongst the different segments.

6. A compound according to claim 5 wherein $R_{73}$, $R_{74}$, $R_{75}$, and $R_{76}$ are hydrogen.

* * * * *